United States Patent [19]

Engel

[11] Patent Number: 5,725,803
[45] Date of Patent: Mar. 10, 1998

[54] WATER/OIL MIXED EMULSIFIER, AS WELL AS THE USE THEREOF IN COSMETIC AND PHARMACEUTICAL FORMULATIONS

[75] Inventor: Walter Engel, Pinneberg, Germany

[73] Assignee: Kawes S.L., Barcelona, Spain

[21] Appl. No.: 736,463

[22] Filed: Oct. 24, 1996

[30] Foreign Application Priority Data

Oct. 24, 1995 [DE] Germany .............. 195 39 429.1

[51] Int. Cl.$^6$ ...................................... B01F 17/30
[52] U.S. Cl. .................. 252/312; 252/89.1; 252/108; 252/132; 252/351; 252/356; 252/363.5; 252/DIG. 5; 252/DIG. 13
[58] Field of Search .................. 252/89.1, 108, 252/132, 312, 351, 356, 363.5, DIG. 5, DIG. 13

[56] References Cited

U.S. PATENT DOCUMENTS 4,218,334   8/1980   Lundmark .
4,391,732   7/1983   Lundmark .

FOREIGN PATENT DOCUMENTS 26 23 927 C2  12/1976  Germany .
26 03 803 A1   8/1977  Germany .
41 25 332 A1   2/1993  Germany .

*Primary Examiner*—John M. Cooney, Jr.
*Attorney, Agent, or Firm*—Merchant, Gould, Smith, Edell, Welter & Schmidt, P.A.

[57] ABSTRACT

The invention relates to a water/oil mixed emulsifier having a content of C-10 to C-28 fatty alcohols, as well as the use thereof in cosmetic and pharmaceutical formulations. The emulsifier contains
a) 6 to 13 wt. % phytosterols;
b) 5 to 23 wt. % C-20 to C-24 2-alkyl alcohols; and
c) a mixture of C-10 to C-28 n-fatty alcohols with the following composition:
  C-10: 0.0 to 1.0 wt. %
  C-12: 1.0 to 3.0 wt. %
  C-14: 12.0 to 16.0 wt. %
  C-16: 16.0 to 21.0 wt. %
  C-18: 11.0 to 14.5 wt. %
  C-20: 6.0 to 10.0 wt. %
  C-22: 7.0 to 11.0 wt. %
  C-24: 2.5 to 5.0 wt. %
  C-26: 0.5 to 2.5 wt. %
  C-28: 0.5 to 1.1 wt. %

8 Claims, No Drawings

WATER/OIL MIXED EMULSIFIER, AS WELL AS THE USE THEREOF IN COSMETIC AND PHARMACEUTICAL FORMULATIONS

BACKGROUND OF THE INVENTION

The present invention relates to a water/oil mixed emulsifier with a C-10 to C-28 fatty alcohol content, as well as the use thereof in cosmetic and pharmaceutical formulations.

The use of water/oil emulsifiers as the sole or additional emulsifier in the preparation of cosmetic and pharmaceutical formulations, such as ointments, creams, lotions, or salves, and also as the superfatting component in cosmetic and pharmaceutical cleaning agents such as soaps, shampoos, and bath lotions, is known. For example, according to the German Pharmacopoeia (DAB), 3.0 wt. % wool wax alcohols and 0.25 wt. % cetyl stearyl alcohol can be processed with approximately 46 wt. % Vaseline and 50 wt. % water to make an aqueous ointment.

Water/oil emulsifiers based on tanolin or wool wax alcohols are prepared from wool fat and contain, apart from steroids and triterpene alcohols, straight and branched-chain C-12 to C-28 alcohols. The preparation of these emulsifiers is very complicated. In addition, in the case of wool fat alcohols and lanolin, it is not possible to exclude a potential for an allergic reaction. The quality of such products is also not constant due to the emulsifier's origin from animal material. Other water/oil emulsifiers based on pentaerythritol fatty acid esters, salts of higher fatty acids, sorbitan fatty acid esters, phytosterols, cholesterol, etc. give rise to stability problems.

Phytosterols have been used as emulsifiers for cosmetic emulsions. However, they have a relatively high melting point, approximately 136° to 140° C. To promote easier processing, 10–50 wt. % of phytosterols is mixed with 50–90 wt. % of a single, free, saturated C-12 to C-18 alcohol. Dodecyl alcohol cetyl alcohol, myristyl alcohol or stearyl alcohol are examples of such alcohols. The incorporation of the separate components into an emulsifier, as well as the subsequent processing with a mineral oil, are facilitated by this process. However, the content of expensive phytosterols is too high and the emulsifying characteristics are inadequate.

Another preparation of a clear, liquid emulsifier concentrate comprises a mixture of 7–15 wt. % sterols or wool wax alcohols with 85–93 wt. % of a branched, saturated C-16 to C-20 alcohol such as highly branched 2-hexyl decanol or 2-octyl decanol. These water/oil emulsifier concentrates, for use in standard cosmetic or pharmaceutical formulations, have a proportion of wool wax alcohols or sterols that is relatively high; leading to end products that are not cost effective.

There is a need for a water/oil mixed emulsifier which has consistent purity, emulsifying power and emulsion stability superior to natural products such as lanolin; which is free from animal and mineral fats and oils, as well as wax esters such as lanolin; and which is a nonionic and EO-free (i.e. epoxi-group free) emulsifier that has properties, such as a low melting range and good processability, that are similar to those of lanolin alcohol emulsifiers.

SUMMARY OF THE INVENTION

The invention relates to a water/oil mixed emulsifier having a content of C-10 to C-28 fatty alcohols, as well as the use thereof in cosmetic and pharmaceutical formulations. The emulsifier contains a) 6 to 13 wt. % phytosterols;
b) 5 to 23 wt. % C-20 to C-24 2-alkyl alcohols; and
c) a mixture of C-10 to C-28 n-fatty alcohols with the following composition:
C-10: 0.0 to 1.0 wt. %
C-12: 1.0 to 3.0 wt. %
C-14: 12.0 to 16.0 wt. %
C-16: 16.0 to 21.0 wt. %
C-18: 11.0 to 14.5 wt. %
C-20: 6.0 to 10.0 wt. %
C-22: 7.0 to 11.0 wt. %
C-24: 2.5 to 5.0 wt. %
C-26: 0.5 to 2.5 wt. %
C-28: 0.5 to 1.1 wt. %

DETAILED DESCRIPTION OF THE PREFERRED EMBODIMENT

Surprisingly, it is found that an emulsifier comprising a mixture of 6–13 wt. % phytosterols; 15–23 wt. % C-20 to C-24 2-alkyl alcohols; and a mixture of C-10 to C-28 n-fatty alcohols shows a significant increase in emulsifying properties. The mixture of n-fatty alcohols has the following composition:
C-10: 0.0 to 1.0 wt. %
C-12: 1.0 to 3.0 wt. %
C-14: 12.0 to 16.0 wt. %
C-16: 16.0 to 21.0 wt. %
C-18: 11.0 to 14.5 wt. %
C-20: 6.0 to 10.0 wt. %
C-22: 7.0 to 11.0 wt. %
C-24: 2.5 to 5.0 wt. %
C-26: 0.5 to 2.5 wt. %
C-28: 0.5 to 1.1 wt. %.

The components of the emulsifier are mixed by conventional methods such as mixing with a stirring device. The mixture may need to be warmed slightly for complete mixing of the components. All components of this emulsifier can be obtained commercially from well-known companies including Henkel and Conoco.

A mixture of commercially available chain-pure C-10 to C-30 fatty alcohols has adequate emulsifying characteristics, but they are nowhere near as good as those of wool wax alcohols. However, with partial replacement of the C-24 to C-26 n-alcohols by C-20 to C-24 2-alkyl alcohols (i.e. isoalcohols), such as 2-octyl dodecanol and 2-decyl tetradecanol, the emulsifier suitability is significantly improved, so that the proportion of phytosterols in the emulsifier can be reduced.

The invention is demonstrated by the following examples.

EXAMPLE 1

An emulsifier comprising a mixture of C-10 to C-28 fatty alcohols with the following composition was prepared:
C-10: 0.1 wt. %
C-12: 1.6 wt. %
C-14: 14.1 wt. %
C-16: 18.2 wt. %
C-18: 13.1 wt. %
C-20: 8.1 wt. %
C-22: 9.4 wt. %
C-24: 3.5 wt. %

C-26: 1.5 wt. %

C-28: 0.8 wt. %.

Next, 2.8 wt. % C-20 2-octyl dodecanol and 17 wt. % C-24 2-decyl tetradecanol were added to the C-10 to C-28 n-fatty alcohol mixture. The remaining 9.8 wt % of the emulsifier was composed of phytosterols in the following approximate proportions: 60% sitosterol, 34% campesterol and 6% stigmasterol.

EXAMPLE 2

The water/oil mixed emulsifier mixture of example 1 was used to formulate a cream having the following composition:

emulsifier according to example 1: 2.3 wt. % paraffin oil: 4.2 wt. %

Vaseline: 27.8 wt. % water: 65.7 wt. %

The cream prepared with the emulsifier was a white, attractively lustrous, pliable formulation with storage stability between 4°–45° C. The water absorption capacity was approximately 65%.

In comparison, an emulsifier comprising a wool wax alcohol and a cetyl stearyl alcohol, an emulsifier combination considered by others to be optimum, was used in a formulation having the following composition:

wool wax alcohol: 3.0 wt. % cetyl stearyl alcohol: 0.25 wt. %

Vaseline: 46.75 wt. % water: 50.0 wt. %

The resulting ointment had a reduced brightness when compared to the previous product and was disadvantageous from the processing standpoint, because it was necessary to use much more Vaseline, namely 46.75 wt. % compared to 27.8 wt. %, and the water absorption capacity was decreased from 65.7 wt. % in the first product to only 50 wt. % in the second product.

EXAMPLE 3

A water/oil mixed emulsifier corresponding to example 1 was prepared, but the proportion of 2-alkyl alcohols was altered to 3.0 wt. % C-20 2-octyl dodecanol and 16.8 wt. % C-24 2-decyl tetradecanol. The resulting cream was the same as the C-10 to C-28 fatty alcohol-containing cream of example 2 except that it had an even whiter, more lustrous structure.

EXAMPLE 4

A water/oil emulsion with the following composition was prepared:

emulsifier according to example 1: 2.00 wt. %

Mg stearate: 1.50 wt. %

Al stearate: 0.75 wt. % white beeswax: 3.00 wt. %

Vaseline, white (DAB): 5.00 wt. % isopropyl myristate: 5.00 wt. % butyl hydroxytoluene: 0.01 wt. % glycerol: 3.00 wt. % magnesium sulphate: 0.70 wt. % water: 63.00 wt. % preservative, perfume: 1.04 wt. %

This emulsion was very cosmetically pleasing.

EXAMPLE 5

A cosmetic cream with the following composition was prepared:

emulsifier according to example 1: 3.40 wt. % white beeswax: 1.00 wt. %

Vaseline, white (DAB): 3.00 wt. % microwax: 1.00 wt. % paraffin oil, viscous (DAB): 3.00 wt. % isopropyl myristate: 10.00 wt. % cetearyl isononanoate—"Cetiol SN": 8.00 wt. % glycerol: 4.00 wt. % magnesium sulphate: 0.70 wt. % water: 64.00 wt. % preservative, perfume: 1.90 wt. %

This cream had particularly good cosmetic characteristics and can, for example, be used as a night cream.

EXAMPLE 6

A toilet soap having superfatting properties with the following composition was prepared:

basic soap: 98.29 wt. % emulsifier according to example 1: 0.39 wt. % dye: 0.01 wt. % antioxidant: 0.05 wt. % perfume: 1.07 wt. % titanium dioxide: 0.19 wt. %

The basic soap consisted of sodium curd soap with approximately 20% water and approximately 78% talc and coconut oil fatty acids. This soap was characterized by a particularly fine foam and an excellent skin feel.

EXAMPLE 7

A soft foam bath additive (tube product) with the following composition was prepared:

lauryl ether sulphate (70%): 40.00 wt. % oleic acid diethanol amide: 4.00 wt. % ethylene glycol stearate: 4.00 wt. % emulsifier according to example 1: 0.50 wt. % isopropyl myristate: 5.00 wt. % sodium chloride: 5.00 wt. % water: 40.00 wt. % preservative, perfume: 1.50 wt. %

This foam bath additive was a pliable, stable, creamy formulation. When correctly used, both on the skin and as a hair treatment, it had a soft, stress-free skin feel.

The above specification, examples and data provide a complete description of the manufacture and use of the composition of the invention. Since many embodiments of the invention can be made without departing from the spirit and scope of the invention, the invention resides in the claims hereinafter appended.

I claim:

1. A water/oil mixed emulsifier comprising a mixture of:

i) a mixture of C-10 to C-28 n-fatty alcohols with the following composition based on the total weight of the emulsifier:

C-10: 0.0 to 1.0 wt. %

C-12: 1.0 to 3.0 wt. %

C-14: 12.0 to 16.0 wt. %

C-16: 16.0 to 21.0 wt. %

C-18: 11.0 to 14.5 wt. %

C-20: 6.0 to 10.0 wt. %

C-22: 7.0 to 11.0 wt. %

C-24: 2.5 to 5.0 wt. %

C-26: 0.5 to 2.5 wt. %
C-28: 0.5 to 1.1 wt. %;

ii) a mixture of C-20 to C-24 2-alkyl alcohols in a quantity of 5 to 23 wt. %; and iii) phytosterols in a quantity of 6 to 13 wt. %.

2. The water/oil mixed emulsifier of claim 1, wherein the phytosterols comprise 50 to 85 wt. % sitosterol, 6 to 40 wt. % campesterol and 0.1 to 10 wt. % stigmasterol, based on the total weight of the phytosterol portion of the emulsifier.

3. The water/oil mixed emulsifier of the claim 1, wherein the mixture of C-20 to C-24 2-alkyl alcohols comprises 2.0 to 3.5 wt. % C-20 2-alkyl alcohol and 15.0 to 19.0 wt. % C-24 2-alkyl alcohol, based on the total weight of the emulsifier.

4. The water/oil mixed emulsifier of claim 3, wherein the mixture of C-20 to C-24 2-alkyl alcohols comprises 2.8 to 3.0 wt. % C-20 2-alkyl alcohol and 16.9 to 18.00 wt. % C-24 2-alkyl alcohol, based on the total weight of the emulsifier.

5. The water/oil mixed emulsifier of claim 4, wherein the C-20 2-alkyl alcohol is 2-octal dodecanol and the C-24 2-alkyl alcohol is 2-decyl tetradecanol.

6. The water/oil mixed emulsifier of claim 1, wherein the mixture of C-10 to C-28 n-fatty alcohols includes the following based on the total weight of the emulsifier:
C-10: <1.0 wt. %
C-12: 1.2 to 2.1 wt. %
C-14: 13.4 to 15.4 wt. %
C-16: 17.7 to 19.5 wt. %
C-18: 12.9 to 13.8 wt. %
C-20: 7.6 to 9.0 wt. %
C-22: 8.8 to 10.5 wt. %
C-24: 2.9 to 4.3 wt. %
C-26: 1.0 to 2.0 wt. %
C-28: 0.6 to 1.0 wt. %.

7. A formulation comprising the water/oil mixed emulsifier of claim 1 for use as an ointment, salve, cream, lotion, soap, shampoo or bath additive.

8. An ointment, salve, cream, lotion, soap, shampoo, or bath additive comprising the water/oil mixed emulsifier of claim 1.

* * * * *

UNITED STATES PATENT AND TRADEMARK OFFICE
CERTIFICATE OF CORRECTION

PATENT NO. : 5,725,803
DATED : MARCH 10, 1998
INVENTOR(S) : ENGEL

It is certified that error appears in the above-identified patent and that said Letters Patent is hereby corrected as shown below:

Cover Page, [73] Assignee: "Kawes" should read --KAWES--

Col. 1, line 20: "tanolin" should read --lanolin--

Signed and Sealed this

Twentieth Day of July, 1999

Attest:

Q. TODD DICKINSON

Attesting Officer

Acting Commissioner of Patents and Trademarks